US010539564B2

(12) United States Patent
Berka et al.

(10) Patent No.: US 10,539,564 B2
(45) Date of Patent: Jan. 21, 2020

(54) IDENTIFICATION OF ANTIGEN EPITOPES AND IMMUNE SEQUENCES RECOGNIZING THE ANTIGENS (71) Applicant: Roche Molecular Systems, Inc., Pleasanton, CA (US)

(72) Inventors: Jan Berka, Pleasanton, CA (US); Sri Paladugu, Mountain House, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/201,689

(22) Filed: Nov. 27, 2018

(65) Prior Publication Data

US 2019/0178886 A1 Jun. 13, 2019

Related U.S. Application Data (63) Continuation-in-part of application No. 15/216,527, filed on Jul. 21, 2016, now Pat. No. 10,168,328.

(60) Provisional application No. 62/195,441, filed on Jul. 22, 2015.

(51) Int. Cl.
| G01N 33/566 | (2006.01) |
| G01N 33/68 | (2006.01) |
| C12N 15/10 | (2006.01) |
| C12Q 1/6809 | (2018.01) |
| C12Q 1/6883 | (2018.01) |

(52) U.S. Cl.
CPC ....... *G01N 33/566* (2013.01); *C12N 15/1037* (2013.01); *C12N 15/1065* (2013.01); *C12N 15/1096* (2013.01); *C12Q 1/6809* (2013.01); *C12Q 1/6883* (2013.01); *G01N 33/6878* (2013.01); *C12Q 2600/158* (2013.01); *G01N 2333/7051* (2013.01)

(58) Field of Classification Search
None
See application file for complete search history.

(56) References Cited

U.S. PATENT DOCUMENTS

| 8,236,503 B2 | 8/2012 | Faham et al. |
| 8,628,927 B2 | 1/2014 | Faham et al. |
| 8,748,103 B2 | 6/2014 | Faham et al. |
| 8,795,970 B2 | 8/2014 | Faham et al. |
| 2010/0330571 A1 | 12/2010 | Robins et al. |
| 2012/0058902 A1 | 3/2012 | Livingston et al. |
| 2013/0303380 A1 | 11/2013 | Ogg |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0255929 A1 | 9/2014 | Zheng |
| 2014/0256567 A1 | 9/2014 | Robins et al. |
| 2014/0322716 A1 | 10/2014 | Robins et al. |
| 2014/0356339 A1 | 12/2014 | Faham et al. |
| 2015/0031043 A1 | 1/2015 | Faham et al. |
| 2015/0031553 A1 | 1/2015 | Faham et al. |
| 2016/0051698 A1 | 2/2016 | Schneck et al. |
| 2016/0298109 A1 | 10/2016 | Ogg et al. |

FOREIGN PATENT DOCUMENTS

| CN | 102443624 B | 12/2014 |
| WO | 2013188471 A3 | 12/2013 |
| WO | 2014055561 A1 | 4/2014 |
| WO | 2014062945 A1 | 4/2014 |
| WO | 2014145992 A1 | 9/2014 |
| WO | 2015/185067 A1 | 12/2015 |

OTHER PUBLICATIONS

Birnbaum, M et al, Deconstructing the Peptide-MHC Specificity of T Cell Recognition, Cell, (2014), pp. 1073-1087, vol. 157, Issue 5.
Han, A. et al, Linking T-cell receptor sequence to functional phenotype at the single-cell level, Nature Biotechnology, (2014), pp. 684-692, vol. 32.
International Search Report dated Oct. 24, 2016 in application No. PCT/EP2016/067284.
Pan, X et al, Combinatorial HLA-peptide bead libraries for high throughput identification of CD8 T cell specificity, Journal of Immunological Methods, (2014), pp. 72-78, vol. 403, Issues 1-2.
Smith, M et al, Highly-multiplexed barcode sequencing: an efficient method for parallel analysis of pooled samples, Nucleic Acids Research, (2010), pp. e142-e142, vol. 38, No. 13.

*Primary Examiner* — Changhwa J Cheu
(74) *Attorney, Agent, or Firm* — Olga Kay

(57) ABSTRACT

Methods, compositions, and reaction mixtures are provided for identifying a T cell receptor (TCR) and an epitope peptide that specifically binds the TCR. Methods, compositions, and reaction mixtures are also provided for identifying a plurality of T cell receptors and corresponding epitope peptides that specifically bind the T cell receptors. In some cases, the plurality of T cell receptors and corresponding epitope peptides can be identified in a highly parallel manner.

2 Claims, 4 Drawing Sheets

Specification includes a Sequence Listing.

Figure 1

1-bead
2-Antigen epitope DNA template
3-Streptavidin
4-StrepTag-MHC
5-DNA encoded peptide
6-Immune receptor (Ig or TCR)
7-Immune cell (B or T cell)

SEQUENCE LISTING

<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tacggactcc gatt

```
<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
accgattagg gaa                                                          13
```

IDENTIFICATION OF ANTIGEN EPITOPES AND IMMUNE SEQUENCES RECOGNIZING THE ANTIGENS

CROSS-REFERENCE TO RELATED APPLICATIONS

This application is a continuation-in-part of the co-pending application Ser. No. 15/216,527 filed on Jul. 21, 2016 which claims priority to the provisional application Ser. No. 62/195,441 filed on Jul. 22, 2015.

SEQUENCE LISTING

The instant application contains a Sequence Listing which has been submitted electronically in ASCII format and is hereby incorporated by reference in its entirety. Said ASCII copy, created on Jul. 19, 2016, is named 32508-US1_SL.txt and is 774 bytes in size.

BACKGROUND OF THE INVENTION

The vertebrate immune system includes adaptive and innate components. The adaptive immune system utilizes effector cells (e.g., B cells and T cells) that express adaptable membrane bound or secreted receptor proteins (e.g., T cell receptors, or B cell receptors or antibodies). For example, T cells can recognize various tumor cells, viruses, or pathogenic organisms through a T cell receptor (TCR). The mammalian immune system can contain $\alpha\beta$ and $\gamma\delta$ TCRs. An $\alpha\beta$ TCR is a heterodimer of an $\alpha$ chain from the TCRA locus and a $\beta$ chain from the TCRB locus. A $\gamma\delta$ TCR is a heterodimer of a $\gamma$ chain from the TCRG locus and a $\delta$ chain from the TCRD locus. These heterodimeric immune recognition receptors recognize epitope peptides presented by the major histocompatibility complex (MHC) class I and II proteins on the surface of antigen-presenting cells (APCs). Binding of TCR to an antigenic epitope peptide on the APC is a central event in T cell activation. This T cell activation can select for T cells that express TCRs with productive binding specificities against tumor or pathogenic antigens.

Each TCR heterodimer contains variable complementarity determining regions (CDRs), as well as framework regions (FRs) and constant regions. The sequence diversity of $\alpha\beta$ T cells is largely determined by the amino acid sequence of the complementarity-determining region (CDR) loops of the $\alpha$ and $\beta$ chain variable domains (CDR1$\alpha$, CDR2$\alpha$, CDR3$\alpha$, CDR1$\beta$, CDR2$\beta$, and CDR3$\beta$). The existence of multiple such gene segments in the TCR $\alpha$ and $\beta$ chain loci allows for a large number of distinct CDR sequences to be encoded. The diversity of CDR3 $\alpha$ and $\beta$ is further increased by recombination between variable (V), diversity (D), and joining (J) gene segments in the $\beta$ chain locus and recombination between V and J gene segments in the $\alpha$ chain locus. CDR3 sequence diversity is also further increased by independent addition and deletion of nucleotides at the V$\beta$-D$\beta$, D$\beta$-J$\beta$, and V$\alpha$-J$\alpha$ junctions during the process of TCR gene recombination.

Similarly, B cells express adaptive immune receptor immunoglobulins (Igs). These immunoglobulins are known as B cell receptors (BCR) when in their membrane bound form and as antibodies when secreted. These immunoglobulins, consist of two heavy chains (H) from the IGH locus and two light chains (L) from either the IGK ($\kappa$) or the IGL ($\lambda$) locus, forming an H2L2 structure. The H and L chains each contain complementarity determining regions (CDR) involved in antigen recognition, and a constant domain. The diversity of naïve Igs within an individual is, in part, determined by the sequence of the hypervariable complementarity determining regions (CDRs). Similar to the TCR, the CDR3 domain of IGH chains is created by the combinatorial joining of the VH, DH, and JH gene segments. Hypervariable domain sequence diversity is further increased by independent addition and deletion of nucleotides at the VH-DH, DH-JH, and VH-JH junctions during the process of Ig gene rearrangement. Ig sequence diversity is further augmented by somatic hypermutation (SHM) throughout the rearranged IG gene after a B cell is activated by antigen recognition. The process of SHM can introduce changes in the germline sequence in framework regions, CDR1 and CDR2, as well as in the somatically rearranged CDR3. Binding of a BCR to an antigenic epitope leads to B cell activation. This B cell activation can select for B cells that express BCRs (and antibodies) with productive binding specificities against tumor or pathogenic antigens.

The resident diversity of CDR, framework, diversity, and joining regions of T cell and B cell receptors combined with diversity enhancing recombination and/or somatic hypermutation results in a vast immune repertoire of antigen binding specificities. Identification of such sequences, and the epitopes to which they specifically bind can be useful, e.g., for (1) guiding the design of recombinant T or B cells for immunotherapy against tumor cells, viruses, or pathogenic organisms; (2) identifying novel antibodies for antibody mediated therapy or development of improved diagnostics; (3) monitoring immune system function and/or disease progression; or (4) detection or quantification of tumor cell or pathogenic organism burden in a host subject.

BRIEF SUMMARY OF THE INVENTION

In a first aspect, the present invention provides a method for identifying a T cell receptor (TCR) and an epitope peptide that specifically binds the TCR, the method comprising: a) providing a plurality of mixture partitions comprising a population of T cells, the T cells comprising a plurality of different TCRs having a TCR heavy chain encoded by a TCR heavy chain nucleic acid and a TCR light chain encoded by a TCR light chain nucleic acid, wherein individual mixture partitions of the plurality of mixture partitions comprise: i) a portion of the population of T cells, wherein the portion of T cells comprises one or more TCRs that specifically bind to a portion of a plurality of epitope peptides present in the mixture partition; ii) a plurality of partition-specific barcodes; and iii) a plurality of epitope nucleic acids encoding the epitope peptides; b) in the plurality of mixture partitions, generating barcoded nucleic acids by attaching the partition-specific barcodes to the TCR heavy chain, TCR light chain, and epitope nucleic acids; c) pooling the barcoded nucleic acids to form a pooled mixture; and d) sequencing the barcoded nucleic acids in the pooled mixture and thereby identifying the sequence of the heavy and light chain of the TCR that specifically binds the epitope peptide and the sequence of the epitope peptide that specifically binds the TCR by identifying heavy and light chain nucleic acids and epitope nucleic acids having matching partition-specific barcodes.

In some embodiments, the method further comprises: e) determining a partition segregation pattern for a plurality of TCR heavy chains, TCR light chains, and epitope peptides by identifying TCR heavy chain nucleic acids that have identical protein coding sequences but different partition-specific barcodes, TCR light chain nucleic acids that have identical protein coding sequences but different partition-specific barcodes, and epitope nucleic acids that have identical protein coding sequences but different partition-specific barcodes; f) classifying TCR heavy chain, TCR light chain, and epitope nucleic acids that co-segregate in a larger number of partitions than expected by chance as encoding a TCR and epitope peptide that specifically bind to each other. In some embodiments, at least one subpopulation of the T cells comprise TCRs having identical TCR heavy chain and TCR light chain nucleic acid sequences.

In some embodiments, the method further comprises f) determining from the partition segregation pattern, the number of partitions in which a TCR heavy chain, a TCR light chain, and an epitope nucleic acids co-segregate; g) applying Formula 1 to determine the probability (P) that the number of partitions in step f) has occurred by random chance; h) classifying the TCR heavy chain, the TCR light chain, and the epitope nucleic acids as encoding a TCR and epitope peptide that specifically bind to each other if probability (P) falls below a preset threshold. In some embodiments, the preset threshold is P=0.05

In some embodiments, the plurality of mixture partitions is a plurality of single cell mixture partitions, and the method comprises classifying barcoded TCR heavy chain, TCR light chain, and epitope nucleic acids that have the same barcode as encoding the TCR and the epitope peptide that specifically binds the TCR. In some embodiments, the providing of claim 1 a) comprises partitioning (T cell):(epitope peptide) complexes into the plurality of mixture partitions in the presence of the plurality of partition-specific barcodes under conditions such that all or substantially all mixture partitions contain no more than one partition-specific barcode sequence. In some embodiments, the providing of a) comprises partitioning (T cell):(epitope peptide) complexes into the plurality of mixture partitions such that all or substantially all mixture partitions contain a different partition-specific barcode sequence, if present.

In some embodiments, the providing of a) comprises partitioning (T cell):(epitope peptide) complexes into the plurality of mixture partitions and then introducing into the mixture partitions the partition-specific barcode nucleic acids. In some embodiments, the plurality of epitope nucleic acids are immobilized on a plurality of solid supports, such that each solid support has a clonal population of immobilized epitope nucleic acids. In some embodiments, the plurality of epitope peptides are immobilized on the plurality of solid supports, such that each solid support has a clonal population of immobilized epitope peptides.

In some embodiments, the clonal population of epitope nucleic acids immobilized on each solid support encodes the clonal population of epitope peptides immobilized on that same solid support. In some embodiments, the epitope peptide nucleic acids further encode a $\beta_2$-microglobulin peptide fused to the epitope peptide. In some embodiments, the epitope peptide is displayed in the context of a major histocompatibility complex class I (MHC class I) protein comprising the $\beta_2$-microglobulin peptide and an MHC class I heavy chain. In some embodiments, the epitope peptides displayed in the context of the MHC class I protein are provided by: a) partitioning a library of solid surface immobilized epitope nucleic acids encoding the epitope peptide fused to the $\beta_2$-microglobulin peptide and a first binding member peptide, wherein the first binding member peptide has affinity for a second binding member immobilized on the solid surface, and wherein each solid surface comprises a clonal population of immobilized epitope nucleic acids; b) in vitro transcribing and translating the immobilized epitope nucleic acids in the partitions, thereby generating a library of solid surface immobilized epitope peptides, wherein each solid surface comprises a clonal population of epitope peptides fused to $\beta_2$-microglobulin peptides and first binding member peptides bound to the second binding member, and wherein each solid surface comprises a clonal population of immobilized epitope nucleic acids that encode the immobilized epitope peptides; and c) refolding the epitope peptides in the presence of MHC class I heavy chain.

In some embodiments, the refolding is performed in the partitions. In some embodiments, the partitions are combined prior to refolding, and the refolding is performed under conditions that do not disrupt the binding between the first and second binding members. In some embodiments, the first and second binding members are independently selected from the group consisting of streptavidin and streptavidin binding protein. In some embodiments, prior to the providing of a), the method comprises contacting the MHC class I displayed epitope peptides with the population of T cells to generate a mixture containing a population of T cells comprising (TCR):(MHC class I displayed epitope peptide) complexes.

In some embodiments, the mixture containing the population of T cells comprising (TCR):(MHC class I displayed epitope peptide) complexes is filtered to remove non-specifically bound and unbound MHC class I displayed epitope peptides if present. In some embodiments, the method further comprises confirming binding between the TCR and epitope peptide by contacting the TCR with the epitope peptide that specifically binds the TCR. In some embodiments, the epitope peptide is displayed in the context of an MHC class I molecule. In some embodiments, the method further comprises detecting the binding by ELISA. In some embodiments, the method further comprises detecting the binding by mass spectrometry. In some embodiments, the method further comprises detecting the binding by flow cytometry.

In a second aspect, the present invention provides a composition comprising a plurality of mixture partitions, wherein individual mixture partitions of the plurality of mixture partitions comprise: a) a T cell having a T cell receptor; b) a major histocompatibility complex class I (MHC class I)-displayed epitope peptide immobilized on a solid surface comprising a nucleic acid encoding the MHC class I displayed epitope peptide; and c) a partition-specific barcode, wherein substantially all partitions contain a unique partition-specific barcode, if present. In some embodiments, the composition comprises a microplate having a plurality of wells, wherein each well comprises a mixture partition, and wherein the plurality of wells is at least 96. In some embodiments, the composition comprises plurality of emulsion droplets, wherein the plurality of emulsion droplets is at least 10,000. In some embodiments, the MHC class I displayed epitope peptide in at least one partition specifically binds at least one TCR in the same partition.

In a third aspect, the present invention provides a reaction mixture comprising: i) a plurality of barcoded T cell receptor (TCR) heavy and light chain nucleic acid sequences; and ii) a plurality of barcoded epitope peptide nucleic acid sequences, wherein the barcoded epitope peptide nucleic acid sequences and the barcoded T cell receptor (TCR) heavy and light chain nucleic acid sequences have identical barcodes.

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4TH ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "partitioning" or "partitioned" refers to separating a sample into a plurality of portions, or "partitions." Partitions can be solid or fluid. In some embodiments, a partition is a solid partition, e.g., a well, a microwell, a nanowell, a channel, a microchannel, a nanochannel, a tube, a microtube, a nanotube, a chamber, a microchamber, a nanochamber, a capsule, a microcapsule, or a nanocapsule. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein, the term "substantially all" in reference to a plurality of mixture partitions or a component of a mixture partition means at least 90%, 95%, 99%, or more.

As used herein, the term "T cell receptor" or "TCR" refers to the antigen recognition complex of a T cell. The TCR is composed of two different protein chains (e.g., alpha and beta or gamma and delta). Each chain is composed of two extracellular domains containing a variable region and a constant region. The variable region contains hypervariable complementarity determining regions (CDRs). Further TCR diversity is generated by VJ (for alpha and gamma chains) and VDJ (for beta and delta chains) recombination. The terms also refer to various recombinant and heterologous forms, including soluble TCRs expressed from a heterologous system.

As used herein, the term "barcode" refers to a nucleic acid sequence that can be detected and identified. Barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides long. Barcodes can employ error correcting codes such that one or more errors in synthesis, replication, and/or sequencing can be corrected to identify the barcode sequence. Examples of error correcting codes and their use in barcodes and barcode identification and/or sequencing include, but are not limited to, those described in U.S. 2010/0,323,348; and U.S. Pat. No. 8,715,967. In some cases, the barcodes are designed to have a minimum number of distinct nucleotides with respect to all other barcodes of a population. The minimum number can be 1, 2, 3, 4, 5, 6, 7, 8, 9, 10, 11, 12, 13, 14, 15, or more. Thus, for example, a population of barcodes having a minimum number of at least 5 distinct nucleotides will differ at at least 5 nucleotide positions from all other barcodes in the population.

As used herein, the term "partition-specific barcode" refers to a barcode having a sequence that uniquely identifies the partition in which it resides or is derived from. The partition-specific barcode can be a single nucleic acid molecule or a clonal population of barcode nucleic acid molecules.

The term "specifically binds to" or "specifically interacts with" in the context of a TCR and a target epitope peptide can refer to an interaction in which the binding between the TCR and the target epitope peptide when displayed in the context of an MHC molecule by an antigen presenting cell can activate a T cell expressing the TCR. The term "specifically binds to" or "specifically interacts with" in the context of a TCR or a BCR and a target epitope peptide can refer to an interaction in which the binding between the TCR or BCR and the epitope peptide is at least 2-fold greater in affinity (e.g., lower Kd) than an interaction between the TCR/BCR and an unrelated or non-target epitope peptide. For example, a TCR that specifically binds a target epitope peptide will typically bind to the target epitope peptide with at least 2-fold (e.g., at least 4-fold, 5-fold, 6-fold, 7-fold, 8-fold, 9-fold, 10-fold, 20-fold, 25-fold, 50-fold, or 100-fold) greater affinity than an epitope peptide that differs in sequence from the target epitope peptide at at least 1, 2, 3, 4, 5, 6, 7, 8, or 9 amino acid positions. The term "specifically binds to" or "specifically interacts with" in the context of a TCR or a BCR and a target epitope peptide can also or alternatively refer to a binding interaction between the peptide and a TCR or a BCR that has a Kd of less than, or less than about, 100 µM, 75 µM, 50 µM, 25 µM, 15 µM, 10 µM, 5 µM, 2 µM, 1 µM, 100 nM, 75 nM, 50 nM, 25 nM, 10 nM, or 1 nM.

The term "epitope peptide nucleic acid" or "epitope nucleic acid" refers to a nucleic acid that encodes an epitope peptide. The nucleic acid can encode other polypeptide molecules in fusion with the epitope peptide, such as an MHC class I heavy chain, $\beta_2$-microglobulin, and a first or second binding member (e.g., streptavidin or streptavidin binding peptide). The epitope nucleic acid can be immobilized on a solid surface such as a bead or a particle. Typically, the epitope nucleic acid encodes an epitope peptide having about 8-17, 8-11, or 13-17 amino acids. In some cases, the epitope peptide has 8, 9, 10, 11, 12, 13, 14, 15, 16, or 17 amino acids. In some cases, the epitope peptide is nine amino acids in length. In some cases, the epitope peptide is a fusion protein containing an epitope, or epitope peptide, region and one or more additional regions (e.g., $\beta_2$-microglobulin, streptavidin, streptavidin binding protein, linkers, etc.). In such cases, the foregoing epitope peptide lengths refer to the epitope peptide region or portion of the epitope peptide fusion protein.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

DETAILED DESCRIPTION OF THE INVENTION

Described herein are methods for identifying a T cell receptor (TCR) and an epitope peptide that specifically binds the TCR. The methods can be performed on a population of T cells for multiplex or highly parallel analysis of the population of TCR specificities. The methods can also be used to probe a population of T cells to identify one or more TCRs that specifically bind to an epitope peptide.

In one embodiment, one or more TCR sequences and the sequence of one or more epitope peptides that are specifically bound by the TCR sequences are determined by contacting an MHC displayed epitope peptide immobilized on a solid surface with a population of T cells to form TCR:epitope peptide complexes. The complexes can be washed or filtered to remove non-specifically bound MHC displayed epitope peptides. The complexes are partitioned into a plurality of single cell partitions and nucleic acids encoding the TCR and epitope peptide in each partition are barcoded with a partition-specific barcode. The partitions are combined and the barcoded nucleic acids are sequenced. Nucleic acid sequences encoding TCRs and epitope peptides that contain matching partition-specific barcodes are identified as encoding a TCR (e.g., $\alpha/\beta$ or $\gamma/\delta$ TCR) and an epitope peptide that form a specific complex.

In another embodiment, T cells are contacted with surface immobilized epitope peptides to form complexes, and optionally washed or filtered, as described above. The complexes are partitioned into a plurality of partitions, wherein each partition contains a partition-specific barcode and a plurality of T cells in complex with one or more epitope peptides. Nucleic acids encoding the TCRs and epitope peptides in each partition are barcoded with a partition-specific barcode. The partitions are combined and the barcoded nucleic acids are sequenced. Nucleic acid sequences encoding TCRs and epitope peptides that contain matching partition-specific barcodes from more partitions than would be likely obtained by chance are identified as encoding a TCR (e.g., $\alpha/\beta$ or $\gamma/\delta$ TCR) and an epitope peptide that form a specific complex.

Methods

TCRs that specifically bind an epitope peptide can be identified by employing a partitioning scheme as outlined herein. A plurality of mixture partitions containing a population of T cells can be provided in which the T cells express a plurality of different (e.g., structurally different) TCRs having a TCR heavy chain encoded by a TCR heavy chain nucleic acid and a TCR light chain encoded by a TCR light chain nucleic acid. The individual mixture partitions of the plurality of mixture partitions can contain i) a portion of the population of T cells, wherein the portion of T cells comprises one or more TCRs that specifically bind to a portion (or all) of the epitope peptides present in the mixture partition; ii) a plurality of partition-specific barcodes; and iii) a plurality of epitope nucleic acids encoding the epitope peptides.

Partitions containing T cells that specifically bind epitope peptides in the partitions can be generated by contacting the T cells with the epitope peptides, removing unbound epitope peptides, and then partitioning the population of T cells and bound epitope peptides. The contacting and/or removing can be performed under conditions suitable to disrupt non-specific binding interactions while retaining specific binding interactions. In some cases, the removing includes filtering a reaction mixture containing epitope peptides (e.g., epitope peptides immobilized on solid supports) and T cells through a membrane containing pores large enough to pass epitope peptides but small enough to retain T cells. Thus, epitope peptides bound to the T cells are retained.

A mixture of epitope peptides in complex with T cells can be partitioned into a plurality of mixture partitions. In some cases, a mixture of epitope peptides in complex with T cells is partitioned into a plurality of mixture partitions containing one or more partition-specific barcodes. In some cases, a mixture of epitope peptides in complex with T cells is partitioned into a plurality of mixture partitions and one or more partition-specific barcodes is introduced into the mixture partitions. In some cases, nucleic acids encoding a mixture of epitope peptides in complex with T cells is partitioned into a plurality of mixture partitions containing one or more partition-specific barcodes. In some cases, nucleic acids encoding a mixture of epitope peptides in complex with T cells is partitioned into a plurality of mixture partitions and one or more partition-specific barcodes is introduced into the mixture partitions.

In some cases, a mixture of epitope peptides in complex with T cells is partitioned into a plurality of mixture partitions and nucleic acids encoding the T cell receptor (TCR) heavy and light chains and the epitope peptides are extracted in the mixture partitions. For example, T cells can be lysed. In some cases, T cells are lysed and nucleic acids therefrom are further purified. In some cases, T cells are lysed and mRNA is further purified. In some cases, mRNA encoding TCR heavy and light chains, or polymerization products therefrom (e.g., cDNA), are purified, e.g., by hybridizing to immobilized TCR capture probes. Similarly epitope peptide nucleic acids can be extracted, purified, and/or amplified. Extracted nucleic acids can be optionally amplified, in vitro transcribed, and/or reverse transcribed. The extracted nucleic acids can then be introduced into a plurality of mixture partitions containing partition-specific barcodes. Alternatively, partition-specific barcodes can be introduced into the mixture partitions containing the extracted nucleic acids. As yet another alternative, partition-specific barcodes can be present in, or introduced into, the mixture partitions prior to extraction of one or more of TCR heavy chain nucleic acid, TCR light chain nucleic acid, or epitope peptide nucleic acid, or a combination thereof.

Partitions containing T cells that specifically bind epitope peptides in the partitions and the epitope nucleic acids that encode such epitope peptides can be obtained by physically linking the epitope peptide and epitope nucleic acid sequences prior to partitioning. In some cases, an epitope peptide and a corresponding epitope nucleic acid that encodes the epitope peptide are physically linked by being bound to the same solid support. Methods, compositions, and reaction mixtures for physically linking epitope peptides and nucleic acids that encode them are described herein.

Alternatively, a population of epitope nucleic acids can be partitioned, optionally transcribed, and translated in the partitions to generate epitope peptides, and then T cells can be partitioned into the partitions containing epitope peptides and the nucleic acids that encode them. The T cells can be incubated under conditions suitable to form TCR:epitope peptide complexes and T cells that do not form specific complexes with epitope peptides in a partition can be segregated. The T cells can be segregated by removing the non-complexed T cells or by moving the epitope peptide complexed T cells to a plurality of new partitions along with the epitope peptide nucleic acids that encode the epitope peptides. Thus, providing partitions containing TCR heavy chain, TCR light chain, and epitope peptide encoding nucleic acids.

In the plurality of mixture partitions, the TCR heavy chain, light chain, and epitope nucleic acids can be attached to partition-specific barcodes. The barcoded nucleic acids so generated can be pooled to form a pooled mixture of barcoded nucleic acids and sequenced. The sequence of the heavy and light chain of the TCR that specifically binds the epitope peptide and the sequence of the epitope peptide that specifically binds the TCR can then be identified on the basis of mixture partition co-segregation, which can be inferred by the presence of matching partition-specific barcodes among a TCR heavy chain, TCR light chain, and epitope nucleic acid.

In some cases, at least one subpopulation of the partitioned population of T cells have identical TCR heavy chain nucleic acid and TCR light chain nucleic acid sequences. For example, the subpopulation of T cells can be a clonal population of T cells having a common origin. Such clonal populations can arise from clonal expansion of T cells activated by binding to an epitope peptide presenting in the context of an MHC by an antigen presenting cell (APC). One or more clonal populations can be generated ex vivo by in vitro T cell expansion. Additionally, or alternatively, one or more clonal populations can be generated in vivo by T cell activation against a tumor cell, virus, pathogenic organism, or antigen therefrom.

In a population of T cells having at least one subpopulation of T cells having identical TCR heavy and light chain nucleic acids, mixture partition co-segregation of identical TCRs and epitope peptides that is greater than expected by random chance can indicate that such a super-co-segregating (co-segregating at a greater frequency than predicted by random chance) TCR and epitope peptide form a specific non-covalent complex. Such super-co-segregating polypeptides can be identified by determining the partition segregation pattern for TCR heavy chains, the partition segregation pattern for TCR light chains, and the partition segregation pattern for epitope peptides and then comparing such segregation patterns (e.g., to identify co-segregating components). The partition segregation pattern for TCR heavy chains can be determined by identifying TCR heavy chain nucleic acids that have identical protein coding sequences but different partition-specific barcodes. Similarly, the partition segregation pattern for TCR light chains and epitope peptides can be determined by identifying TCR light chain nucleic acids and epitope nucleic acids respectively that have identical protein coding sequences but different partition-specific barcodes.

From these partition segregation patterns, TCR heavy and light chain sequences can be identified that co-segregate in a larger number of partitions than can be expected by chance. Such super-co-segregation indicates that the co-segregating TCR heavy and light chain pairs form a TCR expressed by a T cell that specifically binds an epitope peptide in the mixture partitions to which the T cell has been segregated. Similarly, epitope peptides can be identified that co-segregate with such TCR heavy and light chain pairs in a larger number of partitions than can be expected by chance. Such super-co-segregation indicates that the epitope peptide is specifically bound by the similarly super-cosegregating TCR heavy and light chain pair.

In some cases, a large proportion of the binding energy of a TCR:epitope peptide interaction is provided by a single chain, or a single CDR. For example, CDR3 variability is generally highest among the CDRs, due to recombination induced CDR3 variability. CDR3 of the beta chain is, in some cases, the largest contributor to binding energy due to the greater variety of recombination products that can be generated in the beta locus as compared to the alpha locus. Thus, CDR3 or CDR3β can contain, or contribute to, a more highly optimized antigen binding interface as compared to other TCR components of the interface because a larger sequence space is sampled in these regions. In cases where a single TCR chain, or a single CDR sequence contributes a significantly greater proportion of epitope peptide binding energy than other components of the TCR, such sequences can be identified by detecting a greater than random co-segregation of an epitope nucleic acid encoding the epitope peptide and nucleic acids encoding that $\alpha$, $\beta$, $\gamma$, $\delta$, or CDR sequence in the mixture partitions. Thus, detection of super-co-segregation can be used to identify TCR sub-components (e.g., $\alpha$, $\beta$, $\gamma$, $\delta$, or CDR sequences) that contribute to epitope peptide specificity and the corresponding epitope peptide in a population of T cells even in the absence of a clonal population of T cells.

In some cases, the plurality of mixture partitions are single cell mixture partitions. In such cases, co-segregated TCR heavy chain, TCR light chain, and epitope peptides can be identified as corresponding to one or more epitope peptides and a TCR that specifically binds the one or more epitope peptides. Such polypeptides can be identified by detecting heavy chain, light chain, and epitope nucleic acids that have partition-specific barcode sequences that match from the pooled mixture.

Partitions containing partition-specific barcodes can be generated by various methods. For example, a plurality of structurally different barcode nucleic acids can be partitioned from a dilute mixture such that a majority, a substantial majority, substantially all, or all partitions contain 1 or fewer barcode nucleic acids. The barcodes can then be amplified so that identical copies of the barcode can be attached to target nucleic acids (e.g., TCR heavy chain, TCR light chain, and/or epitope peptide encoding nucleic acids) in a mixture partition. As another example, in cases where the number of mixture partitions is less than about $1 \times 10^9$; $1 \times 10^6$; $1 \times 10^5$; 10,000; or 1,000; partition-specific barcodes can be introduced into the mixture partitions manually or via an automated or semi-automated dispensing system. Thus, for example, when the number of mixture partitions is, or is less than about, 1536, 348, 96, 48, 24, 12, or 6, a plurality of solutions containing unique clonal populations of barcodes can be introduced into each mixture partition, e.g., by pipetting or injecting the solution into the mixture partition.

Other methods for obtaining partition-specific barcodes include providing a plurality of solid surfaces, each solid surface containing a clonal population of barcode nucleic acids that are structurally different from the clonal populations of the other solid surfaces. The solid surfaces (e.g., beads) can then be partitioned. Alternatively, a plurality of solid surfaces, each containing a single unique barcode nucleic acid can be partitioned such that a single solid surface is partitioned in each mixture partition, and then amplification of the barcode can be performed in the mixture partitions to generate a clonal population of barcodes in each mixture partition. Exemplary solid surfaces include beads (e.g., polystyrene beads) or gel particles (e.g., polyacrylamide or agarose).

Partitioning of solid surfaces, the individual solid surfaces containing a barcode or a clonal population of a barcode, can allow precise distribution of partition-specific barcodes such that at least 50%, 75%, 80%, 90%, 95%, 99%, 99.5%, 99.9%, or more of the partitions contain only one barcode sequence. Partitioning of solid surfaces, the individual solid surfaces containing a barcode or a clonal population of a barcode, can allow precise distribution of partition-specific barcodes such that at least 50%, 75%, 80%, 90%, 95%, 99%, 99.5%, 99.9%, or more of the partitions contain a barcode sequence. Methods and compositions for generating solid surfaces having unique clonal populations of nucleic acids are described, e.g., in WO/2005/082098.

Attaching of partition-specific barcodes to TCR heavy chain, TCR light chain, and epitope nucleic acids can be performed using a variety of methods and compositions. Such attaching can be performed by ligation, polymerization, or a combination thereof. Attachment by polymerization can be performed by DNA-dependent DNA polymerization (e.g., PCR amplification) or RNA-dependent DNA polymerization (e.g., reverse transcription), or a combination thereof. For example, barcodes can be attached to TCR heavy and light chain nucleic acids via polymerization while barcodes are attached to epitope peptide nucleic acids via ligation, or vice versa. Partition-specific barcodes can be attached to TCR heavy chain, TCR light chain, and/or epitope nucleic acids at one or both ends. In some cases, the barcodes at each end are different. In some cases, the barcodes at each end are the same.

In some cases, attaching of partition-specific barcodes is performed by including the partition-specific barcode into one or more first strand reverse transcription primers. For example, partitions can contain a plurality of first strand reverse transcription primers that contain a partition-specific barcode and an RNA (e.g., mRNA) annealing region. In some cases, the mixture partitions contain a plurality of first strand reverse transcription primers, wherein an individual mixture partition can contain reverse transcription primers having a common partition-specific barcode and different annealing regions to reverse transcribe different target RNA nucleic acids (e.g., mRNA, epitope nucleic acid in vitro transcription product, and/or mRNA encoding TCR heavy and/or light chains). In some cases, the annealing region is a poly-T region that anneals to the poly-A region of mature mRNA. In some cases, the annealing region is a region that specifically hybridizes to a TCR heavy chain nucleic acid, TCR light chain nucleic acid, and/or epitope peptide nucleic acid. For example, the region that specifically hybridizes to a TCR heavy chain nucleic acid can be complementary to a V, J, or C region of a TCR heavy chain nucleic acid. As another example, the region that specifically hybridizes to a TCR light chain nucleic acid can be complementary to a V, J, or C region of a TCR light chain nucleic acid. In some cases, a first strand reverse transcription primer is employed to incorporate an anchor sequence to which a barcoded primer can be annealed and polymerized to incorporate a partition-specific barcode.

In some cases, attaching of partition-specific barcodes is performed by including the partition-specific barcode into a template switching oligonucleotide. The use of template switching oligonucleotides to incorporate barcodes and adaptor sequencing into reverse transcription products is described in, e.g., Harbers et al., BMC Genomics 2013, 14:665. For example, mixture partitions containing a plurality of T cells in complex with epitope peptides, wherein the epitope peptides are physically linked to corresponding epitope peptide nucleic acids, can be subject to conditions to lyse the T cells and release mRNA. The mRNA can be contacted with a first strand reverse transcription primer and a template switching oligonucleotide containing a partition-specific barcode under conditions to permit first strand cDNA synthesis. First strand cDNA synthesis will then incorporate a partition-specific barcode (and/or its complement) into the cDNA product. In some cases, the epitope peptide nucleic acid is RNA or mRNA or is in vitro transcribed into RNA and the partition-specific barcode is attached via reverse transcription of the RNA in the presence of a template switching oligonucleotide. In some cases, a template switching oligonucleotide is employed to incorporate an anchor sequence to which a barcoded primer can be annealed and polymerized to incorporate a partition-specific barcode.

In some cases, partition-specific barcodes are attached by DNA-dependent polymerization. For example, TCR heavy chain nucleic acids, TCR light chain nucleic acids, and epitope peptide nucleic acids can be contacted with one or more DNA-dependent polymerization primers containing partition-specific barcodes and subject to conditions sufficient to permit primer-initiated DNA-dependent polymerization. In some cases, mixture partitions can contain a plurality of primers containing a common partition-specific barcode for each partition and a plurality of different primer hybridization regions. Thus, for example, barcodes can be attached to TCR heavy chain nucleic acids, TCR light chain nucleic acids, and/or epitope peptide nucleic acids in a multiplex reaction. In some cases, partition-specific barcodes are attached by PCR amplification with barcoded primers having partition-specific barcodes.

In some cases, partition-specific barcodes are attached by ligation. For example, adaptors containing partition-specific barcodes can be ligated to TCR heavy chain nucleic acids, TCR light chain nucleic acids, and/or epitope peptide nucleic acids. As another example, adaptors containing an anchor sequence can be ligated to TCR heavy chain nucleic acids, TCR light chain nucleic acids, and/or epitope peptide nucleic acids. Primers containing partition-specific barcodes can then be annealed to the anchor sequence and polymerized to attach partition-specific barcodes.

In some cases, the foregoing nucleic acids are single stranded DNA or RNA nucleic acids, and the adaptors are ligated to the single stranded DNA or RNA. In some cases, the TCR heavy chain nucleic acids, TCR light chain nucleic acids, and/or epitope peptide nucleic acids are treated to repair nucleic acid ends, and/or add dA tails. The inclusion of a single A 3' overhang can increase the efficiency of ligation to adaptors containing a single T overhang.

The nucleic acids can be single stranded DNA (e.g., corresponding to a first strand cDNA product of TCR heavy and/or light chain mRNA). Exemplary methods for ligation of barcodes to single stranded DNA include the ligation of a hairpin adaptor to single stranded DNA. See, Kwok, C. K. et al., Analytical biochemistry, 435(2), 181-186 (2013). The hairpin adaptor can include the partition-specific barcode, or can include an anchor sequence to which a primer containing a partition-specific barcode can then be annealed and polymerized to incorporate a partition-specific barcode.

In some cases, adaptors (e.g., DNA or RNA adaptors) are ligated to single stranded DNA RNA molecules using a DNA/RNA ligase. For example, the 5' AppDNA/RNA Ligase (NEB) can be used to ligate an adaptor to the 3' end of a single stranded DNA or RNA. The DNA or RNA adaptor can contain a partition-specific barcode or can contain an anchor sequence to which a primer containing a partition-specific barcode can then be annealed and polymerized to incorporate a partition-specific barcode.

After attachment of partition-specific barcodes, mixture partitions can be combined and sequenced by high throughput sequencing methodologies. In some cases, additional adaptor and/or indexing (e.g., sample barcoding) sequences are incorporated into target nucleic acids prior to or during preparation of the samples for high throughput sequencing. For example, adaptor sequences specific for Illumina, 454 (Roche), Pacific Biosciences, Life Technologies (Ion Torrent), etc. can be incorporated into the nucleic acids. In some cases, after combining partitions, and optionally attaching additional adaptor and/or barcode sequences to the nucleic acids, a sample can be partitioned again to reduce the complexity of the partitioned sub-samples. In some cases, re-partitioning and further manipulation of the re-partitioned sub-samples can reduce the likelihood or degree of bias introduced in subsequent amplification, polymerization, hybridization, ligation, barcoding, adaptor attachment, or other sample manipulation steps.

In some cases, the T cells in complex with epitope peptides (or nucleic acid therefrom) are partitioned such that at least a majority of such T cells in complex with epitope peptides (or nucleic acid therefrom) are present in a single cell partition having a partition-specific barcode. In such cases, TCR heavy chain, TCR light chain, and epitope peptide nucleic acids from each T cell: epitope peptide complex can be attached to a unique partition-specific barcode for that T cell:epitope peptide complex. After combining of partitions, sequencing of the TCR heavy and light chain and epitope nucleic acids and attached barcodes, or amplicons or polymerization products thereof, indicates the TCR heavy and light chain sequence pair that encodes a complete T cell receptor heterodimer (e.g., alpha and beta chain or gamma and delta chain) that binds to a epitope peptide sequence. For example, TCR heavy and light chain nucleic acids that share the same partition-specific barcode sequence can be identified as encoding a TCR heavy and light chain respectively that form an intact TCR that specifically binds an epitope peptide encoded by an epitope peptide nucleic acid that also shares the same partition-specific barcode sequence. Methods and compositions for partitioning single cells, including single T cells, barcoding single cells, and/or sequencing single cells, include methods in which single cells are partitioned into a plurality of emulsion droplets containing barcoding reagents. Methods and compositions for partitioning single cells, including single T cells, barcoding single cells, and/or sequencing single cells, include those described in U.S. 2013/0,296,565; 2013/0,274,117; WO 2010/117,620; and WO 2015/031,691.

In some cases, the T cells in complex with epitope peptides (or nucleic acid therefrom) are partitioned such that each partition contains a plurality of cells or nucleic acid from a plurality of cells. For example, partitions can contain, contain at least, or contain at least about, 2; 3; 4; 5; 6; 7; 10; 11; 12; 13; 14; 15; 20; 25; 50; 75; 100; 200; 300; 400; 500; 600; 700; 800; 1,000; 2,000; 3,000; 5,000; 7,500; 10,000; 20,000; 25,000; 50,000; 75,000; 100,000; 200,000; 300,000; 400,000; 500,000; 750,000; $1\times10^6$; $1\times10^7$, $1\times10^8$; or $1\times10^9$ cells or nucleic acid therefrom (e.g., on average). In some cases, the T cells in complex with epitope peptides (or nucleic acid therefrom) are partitioned such that each partition contains substantially the same or a similar number of cells or nucleic acid therefrom. For example, each partition can contain a number of cells that is within 1, 2, 3, 4, 5, 6, 7, 8, 9, 10, 11, 12, 13, 14, 15, 16, 17, 18, 19, 20, 21-30, 31-50, 51-70, 71-80, or 81-100 percent of the number of cells in any other partition. Exemplary partitions can be wells of a 6, 12, 24, 48, 96, 384, or 1536 well cell culture plate or any other or any other suitable container that is capable of containing the cells or nucleic acid therefrom.

Cells can be partitioned into the plurality of mixture partitions, such that partitions contain multiple cells, by pipetting, microfluidics, fluorescence activated cell sorting (FACS), or the like. For example, cells can be isolated and sorted according to various criteria, and deposited into a cell culture plate by FACS. In some cases, FACS is used to isolate and sort viable cells by detecting the presence or absence of a vital dye or by measuring forward scattering and/or side scattering, or a combination thereof. In some cases, sub-populations of cells are isolated and partitioned by FACS based on detection of the presence or absence of a cell surface marker, such as a TCR, alpha chain, beta chain, CD30, CD38, CD45RA, CD45RO, CD294, CCR5, CXCR4, one or more of TLR2-5, and the like. In some cases, T cells that are in complex with one or more epitope peptides are isolated, sorted, and partitioned, isolated and partitioned, or partitioned.

After partitioning of cells, cells can be lysed and nucleic acid extracted therefrom. Alternatively, nucleic acid has previously been extracted from partitioned and then lysed T cells and the nucleic acid is transferred to new partitions (e.g., partitions containing partition-specific barcodes or partitions to which partition-specific barcodes are introduced). The nucleic acid (e.g., T cell nucleic acid and/or epitope peptide nucleic acid) can be isolated, purified, reverse transcribed, in vitro transcribed, and/or amplified as previously described. Partition-specific barcodes can be attached as previously described. The partitions can be combined and sequenced as previously described. In some cases, after combining of partitions, the sample is re-partitioned to produce sub-samples of reduced complexity. In some cases, re-partitioning and further manipulation of the re-partitioned sub-samples can reduce the likelihood or degree of bias introduced in subsequent amplification, polymerization, hybridization, ligation, barcoding, adaptor attachment, or other sample manipulation steps.

After sequencing of pooled and barcoded nucleic acid from partitions containing i) a portion of the population of T cells, wherein the portion of T cells comprises one or more TCRs that specifically bind to a portion of epitope peptides present in the mixture partition; ii) a plurality of partition-specific barcodes; and iii) a plurality of epitope nucleic acids encoding the epitope peptides, TCRs that specifically bind epitope peptides can be identified on the basis of the partition segregation patterns of nucleic acids encoding components of the TCR epitope peptide complex. Partition segregation patterns are identified by detecting nucleic acids encoding TCR epitope peptide complex components that share the same partition-specific barcodes, indicating that they derived from the same partition. Detection of multiple events in which structurally identical TCR heavy chain, TCR light chain, and epitope peptide encoding nucleic acids are found to have co-segregated into the same partition indicates an increased likelihood that the co-segregation was due to a specific interaction rather than random chance.

As an example, if a sample of cells in complex with epitope peptides that are each linked to a nucleic acid encoding that epitope peptide is evenly partitioned into 100 wells of a tissue culture plate and partition-specific barcodes are attached to nucleic acids encoding TCR heavy chains, TCR light chains, and epitope peptides, then the chance that a specific combination of TCR heavy chain, TCR light chain, and epitope peptide encoding nucleic acids will randomly share the same partition-specific barcode is $(1\times10^{-2})^3$ or 1 in $10^6$. Therefore, the probability that two structurally identical sets of TCR heavy chain, TCR light chain, and epitope peptide encoding nucleic acids are detected as having independently derived from two different partitions, such that one set shares one partition-specific barcode and the second structurally identical set shares a second partition-specific barcode is 1 in $10^{12}$. Detection of additional structurally identical sets that share additional partition-specific barcodes further indicates decreased likelihood of co-segregation of the set by random chance and therefore an increased likelihood of co-segregation by virtue of having derived from a specific binding interaction between the TCR and the epitope peptide.

The probability of a given T cell:epitope peptide complex occupying a pattern of a certain number of partitions is dependent on three variables: the frequency of a clonal sub-population of T cells (with identical TCRs and identical antigen binding specificity) within the total population of T cells sampled, the number of T cell:epitope peptide complexes in each partition and the total number of barcoded partitions. For example, a sample of $1\times10^7$ T cell:epitope peptide complexes with a clonal frequency of $10^{-6}$ partitioned into wells of a 96-well plate will result in those clones occupying on average 10 wells. In contrast, the probability of two different (non-clonal) T cells occupying the same 10-well pattern depends on the number of unique combinations of 10-wells. For example, on a 96-well plate, there are (96 choose 3) 142,880 unique 3-well combinations and (96 choose 10) $1.13\times10^{13}$ unique 10-well combinations. Thus, the greater the number of wells in which a TCR heavy chain, light chain, and epitope peptide group is detected, the greater the probability that said TCR heavy chain, light chain, and epitope peptide group is a TCR that specifically binds the epitope peptide. Typically, a TCR heavy and light chain and corresponding specifically bound epitope peptide is identified when the sequences encoding such TCR heavy chain, light chain, and epitope peptide are detected as co-segregating into, or into at least, 3, 4, 5, 6, 7, 8, 9, 10, 11, 12, or more partitions.

In some embodiments, the invention comprises a method of determining the statistical probability that a TCR-alpha chain, a TCR-beta chain and an antigen co-segregate into one or more wells non-randomly and due to the fact that the TCR formed by the alpha and beta chains is specific for the antigen. The probability is determined using the total number of wells and the observed number of wells with co-occurrence of a TCRA, a TCRB and an antigen.

In some embodiments, the probability that segregation is random (P) is compared to a cut-off value or a threshold. If the probability of random co-occurrence falls below the cut-off value or a threshold, the observed co-occurrence is non-random. Non-random co-occurrence or co-segregation means that the TCRA and the TCRB form a TCR that is specific for the antigen. In some embodiments, the cut-off value for P is 0.05. In other embodiments, a lower or a higher cut-off value may be used.

In some embodiments, the probability of random segregation (P) is determined using Formula 1 used as follows. Consider the case where there are a total of W distinct wells of which $w_\alpha$ wells are occupied by TCR-alpha sequences, $w_\beta$ wells are occupied by TCR-beta sequences and $w_\delta$ wells are occupied by antigen sequences. If all three sequences share $w_{\alpha\beta\delta}$ wells, then we want to estimate the probability of observing this amount of well sharing by random chance.

The method comprises a step of estimating the probability of observing well sharing in exactly $w_{\alpha\beta\delta}$ wells, conditioned on the fact that there are a total of W wells, wherein TCR-alpha sequences occupy $w_\alpha$ wells, TCR-beta sequences occupy $w_\beta$ wells and antigen sequences occupy $w_\delta$ wells. The step comprises the use of the following formula.

$$P = P(w_{\alpha\beta\delta} \mid W, w_\alpha, w_\beta, w_\delta) = \frac{C(W, w_{\alpha\beta\delta}) \times \begin{vmatrix} (w_\alpha - w_{\alpha\beta\delta}), (w_\beta - w_{\alpha\beta\delta}), \\ (w_\delta - w_{\alpha\beta\delta}), (W - w_{\alpha\beta\delta}) \end{vmatrix}}{C(W, w_\alpha) \times C(W, w_\beta) \times C(W, w_\delta)}$$

FORMULA 1

Wherein:

$C(W, w_\alpha)$ is the number of ways we can choose $w_\alpha$ wells from $W$ wells $\equiv \binom{W}{w_\alpha}$ $C(W, w_\beta)$ is the number of ways we can choose $w_\beta$ wells from $W$ wells $\equiv \binom{W}{w_\beta}$ $C(W, w_\delta)$ is the number of ways we can choose $w_\delta$ wells from $W$ wells $\equiv \binom{W}{w_\delta}$ $C(W, w_{\alpha\beta\delta})$ is the number of ways we can choose $w_{\alpha\beta\delta}$ wells from $W$ wells $\equiv \binom{W}{w_{\alpha\beta\delta}}$ In determining the value of P, the value of A is determined wherein $$A = |(w_\alpha - w_{\alpha\beta\delta}), (w_\beta - w_{\alpha\beta\delta}), (w_\delta - w_{\alpha\beta\delta}), (W - w_{\alpha\beta\delta})|.$$

A is the number of ways we can choose:
$w_\alpha - w_{\alpha\beta\delta}$ wells from $W - w_{\alpha\beta\delta}$ wells and
$w_\beta - w_{\alpha\beta\delta}$ wells from $W - w_{\alpha\beta\delta}$ wells and
$w_\delta - w_{\alpha\beta\delta}$ wells from $W - w_{\alpha\beta\delta}$ wells such that none of the $W - w_{\alpha\beta\delta}$ wells contain all three types of sequences in one well.

Coming up with a closed form solution for the equation for A may utilize several methods. In some embodiments, Sieve Method or Inclusion-exclusion principle is used to compute a numerical value for A. This is demonstrated in Examples 2, 3 and 4 in the EXAMPLES section.

Sequencing of barcoded nucleic acids can be performed using a high throughput sequencing method. Exemplary high throughput sequencing methods that can be used to determine the sequences of barcoded TCR encoding and epitope peptide encoding nucleic acids, including methods and compositions for preparation of samples, methods and compositions for amplification and/or barcoding of nucleic acids, and primer, oligonucleotide, and/or adaptor compositions include but are not limited to those described in, e.g., U.S. 2010/330,571; U.S. 2014/0,235,477; US 2014/057,799; U.S. Pat. Nos. 7,999,092; 8,795,970; 8,691,510; WO 2009/137,255; WO 2010/117,620; WO 2012/048,340; WO 2013/097,744; and WO 2012/083,225, each of which is incorporated by reference in the entirety.

In order for an epitope peptide to complex with a TCR, the epitope peptide must typically be displayed in the context of an MHC molecule. In some embodiments, the epitope peptides are bound to MHC molecules and presented to T cells to form TCR:epitope peptide complexes. In some cases, an epitope peptide is encoded by a nucleic acid that also encodes one or more components of the MHC molecule to which it is complexed. If the epitope peptide encoding nucleic acid is mRNA, the nucleic acid can be translated to generate a polypeptide that includes the epitope peptide and one or more components of the MHC molecule to which it is complexed. If the epitope peptide encoding nucleic acid is DNA, the nucleic acid can be transcribed and the transcription product translated to generate a polypeptide that includes the epitope peptide and one or more components of the MHC molecule to which it is complexed.

In some cases, the epitope peptide nucleic acids each encode an epitope peptide and a $\beta_2$-microglobulin domain. Alternatively, in some cases, the epitope peptide nucleic acids each encode an epitope peptide and an MHC class I heavy chain. In some cases, each epitope peptide nucleic acid encodes the same MHC class I heavy chain. The use of a constant heavy chain can eliminate variability in peptide recognition by TCRs that is due to the MHC molecule. Alternatively, different epitope nucleic acids can encode different MHC class I molecules. Thus, variability in peptide recognition by TCRs that is due to the identity of the MHC molecule can be examined.

Epitope peptides displayed in the context of an MHC class I protein can be provided by: a) partitioning a library of epitope nucleic acids encoding an epitope peptide and a $\beta_2$-microglobulin domain; b) in vitro transcribing and translating the epitope peptide nucleic acids in the partitions, thereby generating a library of epitope peptides fused to $\beta_2$-microglobulin, and refolding the epitope peptides in the presence of MHC class I heavy chain. In some cases, the library of epitope nucleic acids is a library of nucleic acids immobilized on a plurality of solid surfaces such that each solid surface has a clonal (or substantially clonal) population of epitope nucleic acids.

In some embodiments, the epitope nucleic acids further encode a first binding member, such that in vitro transcribing and translating the epitope peptide nucleic acids in the partitions, thereby generates a library of epitope peptides fused to $\beta_2$-microglobulin and the first binding member. In some cases, the first binding member has a specific affinity for a second binding member on a solid surface to which the epitope nucleic acid is immobilized. The first and second binding members can be independently selected from streptavidin and streptavidin binding protein. For example, epitope nucleic acids can encode epitope peptide, $\beta_2$-microglobulin, and streptavidin binding protein and be immobilized on solid surfaces that contain streptavidin. In vitro transcribing and translating the epitope peptide nucleic acids in the partitions can thereby generate a library of epitope peptides fused to $\beta_2$-microglobulin and streptavidin binding protein. The streptavidin binding protein:streptavidin interaction can thereby immobilize the translation product of the epitope nucleic acid. Other suitable first and second binding member pairs can be readily determined by those of skill in the art.

In some cases, the translation is performed such that structurally different epitope nucleic acids are translated in different partitions. In such cases, then the epitope peptide and the nucleic acid encoding such peptide can be physically linked to the same solid surface. Re-folding of the epitope peptides with MHC class I heavy chain can then provide a library of epitope peptides, wherein the epitope peptides are displayed in the context of an MHC class I molecule and physically linked to the nucleic acids that encode the epitope peptides.

In some cases, the refolding is performed in partitions. Refolding epitope peptides in the presence of an MHC class I heavy chain in partitions, such that structurally different epitope peptides are in different partitions, can ensure that the resulting epitope peptide MHC class I complex is bound to the solid surface to which the epitope nucleic acid that encodes the epitope peptide is immobilized. Alternatively, the refolding can be performed after combining of partitions under conditions that do not, or do not substantially, disrupt the interaction between the first binding member and the second binding member. Thus, once the epitope peptide and encoding epitope nucleic acid immobilized on a solid surface are physically linked after translation of the epitope nucleic acid, or an in vitro transcription product thereof, by a first and second binding member interaction, the physical linkage can be maintained by avoiding conditions that disrupt the first and second binding member interaction.

Refolding can be performed such that each epitope peptide is refolded in the presence of the same MHC class I heavy chain, resulting in epitope peptides displayed in the context of a constant MHC class I molecule. The use of a constant MHC can eliminate variability in peptide recognition by TCRs that is due to the MHC molecule. Alternatively, refolding can be performed with different MHC class I molecules. Thus, variability in peptide recognition by TCRs that is due to the identity of the MHC molecule can be examined.

Methods and compositions for forming partitions containing a clonal population of solid surface immobilized epitope peptides, a clonal population of solid surface immobilized epitope peptides displayed in the context of an MHC class I molecule, and/or a clonal population of epitope peptides that are immobilized on a solid surface containing an epitope nucleic acid that encodes that epitope peptide are described in Pan et al., J. Immunol. Methods, 403 (2014) 72-78. Pan et al. (2014) further describe methods and compositions for forming and isolating TCR:epitope peptide complexes in which the epitope peptides are displayed in the context of an MHC class I molecule and physically linked to the epitope nucleic acid that encodes the epitope peptide.

In some embodiments, identification of TCR heavy and light chain pairs that form a TCR that specifically binds an epitope peptide by detecting the presence of a common partition-specific barcode on nucleic acids encoding the TCR heavy and light chains and the epitope peptide or by detecting a greater than expected co-segregation of TCR heavy and light chain and epitope peptide nucleic acids via partition-specific barcodes can be confirmed by detecting or measuring binding between the corresponding TCR and epitope peptide. For example, a T cell having a TCR that has been identifying as binding a corresponding epitope peptide can be isolated, obtained, provided, or generated (e.g., by transforming the T cell or a progenitor thereof with the TCR heavy and light chain encoding nucleic acids). The T cell can be contacted with the candidate epitope peptide and binding can be confirmed. The binding can be confirmed by ELISA, RIPA, mass spectrometry, flow cytometry, and the like. In some cases, the epitope peptide is displayed by an antigen presenting cell and binding is confirmed by detecting T cell activation.

Alternatively, a soluble or secreted form of the TCR can be provided and binding with an epitope peptide can be performed. For example, TCR heavy and light chain encoding nucleic acids (e.g., nucleic acids encoding truncated TCR heavy and light chains lacking a transmembrane region) can be expressed in a heterologous system and the TCR peptides purified as inclusion bodies and refolded to form a soluble TCR. In some cases, the TCR heavy and light chains are expressed, and optionally purified, from different cells and then refolded. In some cases, the TCR heavy and light chains are expressed in the same cell. As another example, nucleic acids encoding TCR heavy and light chains that lack a transmembrane region can be expressed in a heterologous system and secreted into conditioned medium as a soluble TCR. The soluble TCR can then be assayed for binding to an epitope peptide (e.g., an epitope peptide displayed in the context of an MHC molecule) by ELISA, RIPA, mass spectrometry, flow cytometry, and the like. In some cases, the epitope peptide is displayed by an antigen presenting cell and binding is confirmed by detecting T cell activation.

Compositions

Described herein are compositions for determining specificity of a TCR, identifying TCRs that specifically bind an epitope peptide sequence, and compositions for high throughput characterization of the specificity of a population of TCRs for a population of epitope peptides. In some embodiments, the composition comprises a plurality of mixture partitions, wherein individual mixture partitions of the plurality contain a) one or more T cells having T cell receptors; b) an MHC displayed epitope peptide immobilized on a solid surface that containing a nucleic acid encoding the MHC displayed epitope peptide; and c) a partition-specific barcode, wherein substantially all partitions contain a unique partition-specific barcode, if present.

In some cases, the partitions are wells. For example, the partitions can be wells of a 6, 12, 24, 48, 96, 384, or 1536 well cell culture or microplate. In some cases, the composition contains at least about 6, 12, 24, 48, 96, 384, or 1536 wells. In some cases, the composition contains less than about 6, 12, 24, 48, 96, 384, or 1536 wells. In some cases, the composition contains from 6 to 1536 wells. In some cases, the composition contains from 12 to 96, 384, or 1536 wells. In some cases, the composition contains from 24 to 96 wells.

In some cases, the partitions are microdroplets, such as emulsion droplets. For example, the composition can contain at least 100; 500; 1,000; 2,000; 5,000; 7,500; 10,000; 15,000; 20,000; 30,000; 50,000; 75,000; 100,000; 150,000; 175,000; 200,000; 500,000; 750,000; or 1×10$^6$, or more emulsion droplets. In some cases, the composition contains from 10,000 to 30,000 emulsion droplets.

In some cases, the composition contains at least one partition in which an MHC class I displayed epitope peptide specifically binds at least one TCR in the same partition. In some cases, the composition contains at least two partitions in which an MHC class I displayed epitope peptide specifically binds at least one TCR in the same partition. In some cases, a majority, or at least 50%, 60%, 70%, 80%, 90%, 95%, 99%, or more of the partitions of the composition contain at least one MHC class I displayed epitope peptide that specifically binds at least one TCR in the same partition. At least a majority of partitions containing T cells forming a specific interaction with epitope peptides therein can be obtained by, e.g., isolating T cells that are in complex with MHC class I displayed epitope peptides before partitioning, or removing uncomplexed T cells after partitioning.

Also described herein is a reaction mixture containing i) a plurality of barcoded T cell receptor (TCR) heavy and light chain nucleic acid sequences; and ii) a plurality of barcoded epitope peptide nucleic acid sequences, wherein barcoded TCR heavy and light chain nucleic acid sequences having the same barcode have an increased probability of encoding a TCR that specifically binds an epitope peptide encoded by an epitope nucleic acid sequence having the same barcode as compared to TCR heavy and light chain and epitope peptide nucleic acids having different barcodes.

EXAMPLES

Example 1: Partitioning T-Cells with Antigens and Generating Barcoded Sequences

Figure 1:
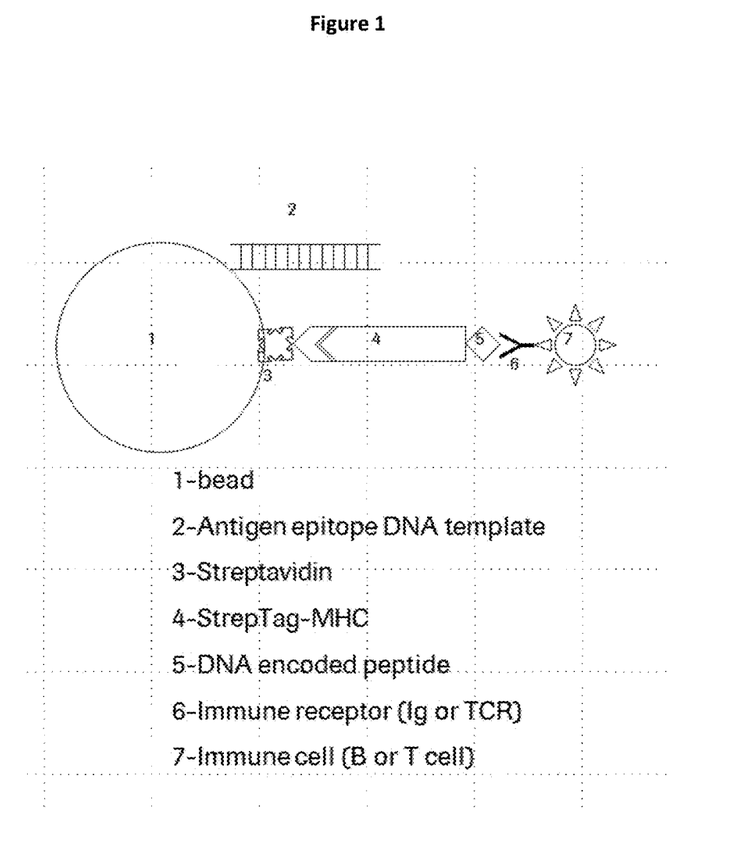
FIG. 1: depicts an illustration of a peptide antigen bead library (1-5) bound to an immune cell (T or B cell) via an immune receptor (Ig or TCR).

A library of peptide:antigen beads bound to T cell displayed TCRs as depicted in FIG. 1 is generated as follows. A plurality of solid surface bead particles (1) comprising surface immobilized streptavidin (3) are partitioned into a plurality of partitions such that each partition contains a epitope peptide encoding nucleic acid and a bead. The epitope peptide encoding nucleic acid comprises a promoter operably linked to a $\beta_2$-microglobulin encoding sequence, the epitope peptide encoding sequence, and a streptavidin binding peptide sequence. Partitions further contain primers for PCR amplification of the epitope peptide encoding nucleic acid, wherein at least one of the primers is biotinylated. PCR amplification is performed in the partitions (e.g., using conditions described in Diehl et al. Nature Methods 3, 551-559 (2006) and/or Pan et al. J. Immunol. Methods 403 (2014) 72-8), thereby generating a biotinylated double stranded epitope peptide encoding nucleic acid (2), wherein said biotinylated double stranded epitope peptide encoding nucleic acid is immobilized on the surface of the bead via surface immobilized streptavidin. The partitions are combined and re-partitioned into a plurality of partitions with in vitro transcription translation reagents to transcribe and translate the epitope peptide encoding nucleic acid into a polypeptide comprising streptavidin binding protein and $\beta_2$-microglobulin, and the epitope peptide (5). The translated product binds to the surface immobilized streptavidin via the streptavidin binding protein. The partitions are combined and the $\beta_2$-microglobulin expressing beads are refolded with HLA heavy chain to generate an intact MHC protein (4). The beads are incubated with a population of immune receptor (6) expressing T cells or B cells (7) to form a library of the bead complexes depicted in FIG. 1.

Figure 2:
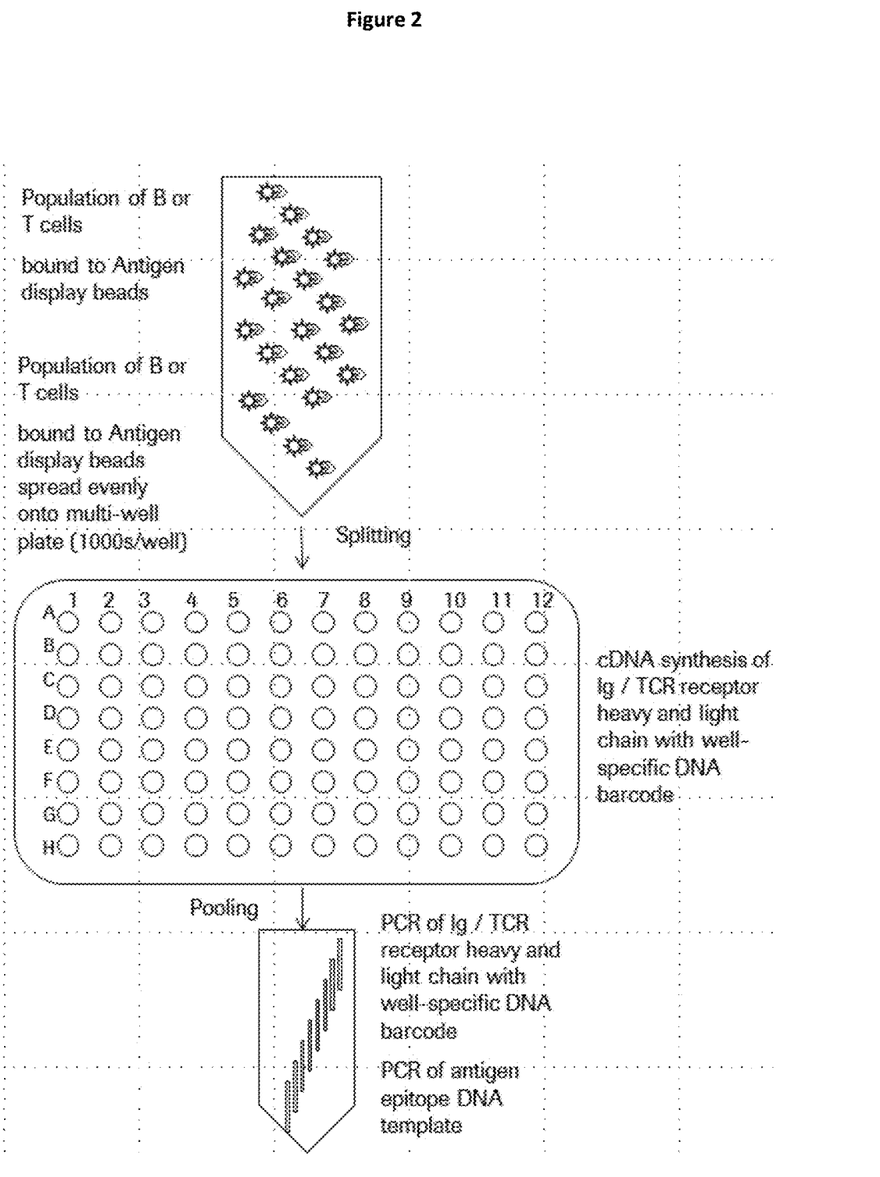
FIG. 2: depicts a method of multi-well plate combinatorics to identify antigen receptor complexes.

The library is evenly partitioned into a 96 well plate such that 1000s of bead complexes are present in each well. The wells contain partition specific barcode primers. cDNA synthesis is performed under conditions such that the epitope peptide encoding nucleic acids, and TCR and/or BCR encoding nucleic acids are tagged with partition specific barcode sequences. After cDNA synthesis and barcoding, the cDNAs are pooled and subject to high throughput sequencing (FIG. 2).

Figure 3:
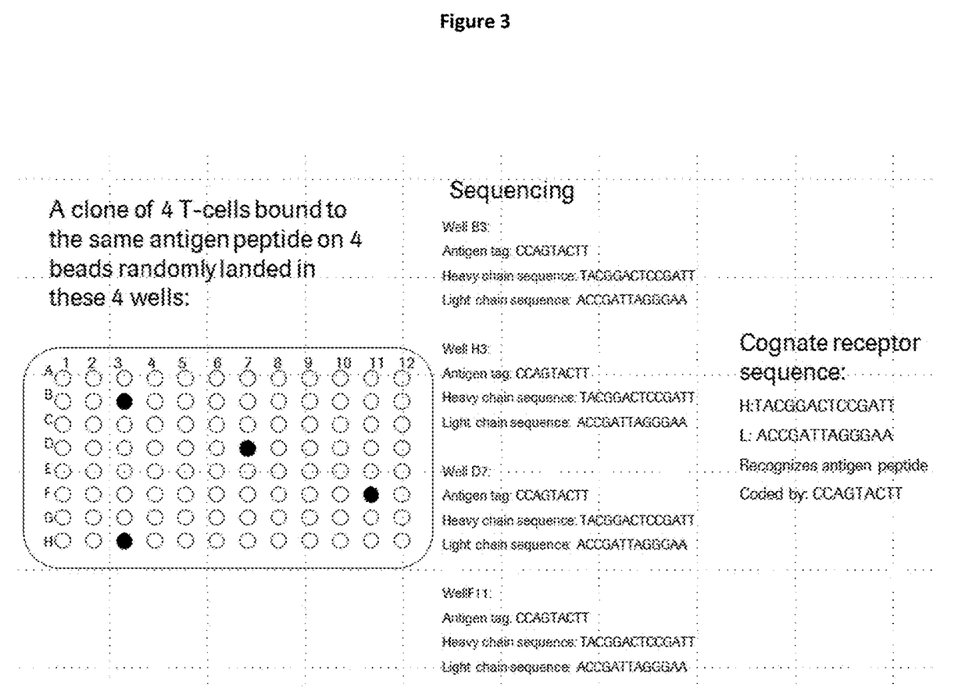
FIG. 3: depicts a bioinformatics method for reconstitution of matching barcode patterns. Figure discloses "Heavy chain sequence" as SEQ ID NO: 1 and "Light chain sequence" as SEQ ID NO: 2.

FIG. 3 illustrates an exemplary result in which a clonal population of 4 T cells bound to the same antigen peptide on 4 different beads randomly segregated into four different wells. The four different TCR heavy chain, TCR light chain, and epitope peptide encoding nucleic acid co-segregation events are detected by detecting four distinct events in which a partition specific barcode sequence is shared amongst co-segregating TCR heavy chain, TCR light chain, and epitope peptide encoding nucleic acid. The detection of 4 different co-segregation events indicates with a high probability that the co-segregating TCR heavy chain, TCR light chain, and epitope peptide encoding nucleic acids encode a TCR that specifically binds the epitope peptide.

Example 2: Calculating the Probability of Random Co-Occurrence in 1/100 Wells In this Example, there is a plate with 100 wells wherein we observed 2 wells with TCR-Alpha sequences, 2 wells with TCR-Beta sequences and 2 wells with Antigen sequences. If we observed well sharing by all 3 types of sequences in 1 of those wells, then we want to estimate the probability of seeing this amount of well sharing just by chance.

| W0 | W1 | W2 | ... | W99 | W100 |
|----|----|----|-----|-----|------|

$$P(w_{\alpha\beta\delta} = 1 \mid W = 100, w_\alpha = 2, w_\beta = 2, w_\delta = 2) =$$

$$\frac{\binom{100}{1} \times \left(\binom{99}{1} \times \binom{99}{1} \times \binom{99}{1} - \binom{99}{1}\right)}{\binom{100}{2} \times \binom{100}{2} \times \binom{100}{2}} = 0.0008$$

Because the observed value of P is smaller than the cut-off value of P=0.05, the TCRA and the TCRB in this example form a TCR specific for the Antigen.

Example 3: Calculating the Probability of Random Co-Occurrence in 2/100 Wells In this example, there is a plate with 100 wells wherein we observed 2 wells with TCRA sequences, 2 wells with TCRB sequences and 2 wells with Antigen sequences. If we observed well sharing by all 3 types of sequences in 2 of those wells, then we want to estimate the probability (P) of seeing this amount of well sharing just by chance.

| W0 | W1 | W2 | ... | W99 | W100 |
|----|----|----|-----|-----|------|

$$P(w_{\alpha\beta\delta} = 2 \mid W = 100, w_\alpha = 2, w_\beta = 2, w_\delta = 2) =$$

$$\frac{\binom{100}{2}}{\binom{100}{2} \times \binom{100}{2} \times \binom{100}{2}} = 4.0812162 \times 10^{-8}$$

Because the observed value of P is smaller than the cut-off value of P=0.05, the TCRA and the TCRB in this example form a TCR specific for the Antigen.

Figure 4:
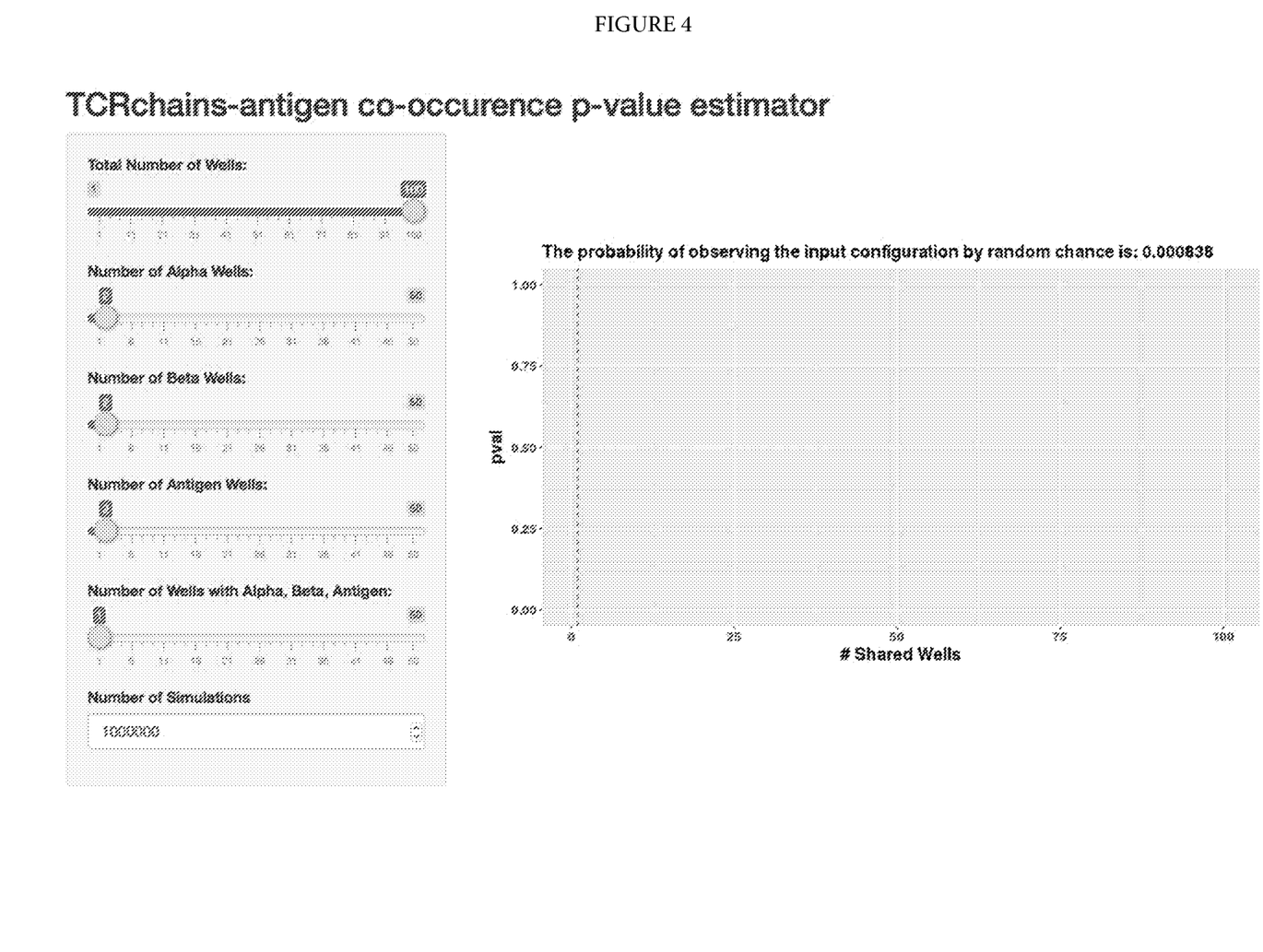
FIG. 4: depicts a simulation experiment to observe co-occurrence of the TCR sequences and Antigen sequences.

Example 4: Using Simulation of Non-Random Co-Occurrence of TCR and Antigen Sequences In this example, simulation is used to calculate the probability of well-sharing by a set of three sequences by random chance given a well configuration as shown in Example 2. FIG. 4 illustrates that the probability of random co-occurrence obtained by simulation closely matches that obtained by numerical method. In this example, simulation is used to calculate the probability of well-sharing by a set of three sequences by random chance given a well configuration as follows: Total number of wells in the plate is 100, TCR-Alpha sequences were observed in 30 wells, TCR-Beta sequences were observed in 30 wells, Antigen sequences were observed in 30 wells and 5 wells are occupied by all three types of sequences.

The FIG. 4, left sub-panel in the graphical user interface allows the user to set the simulation parameters: Total number of Wells i.e., number of wells in the plate (W), Number of Alpha Wells i.e., number of wells occupied by alpha sequences ($w_\alpha$), Number of Beta Wells i.e., number of wells occupied by beta sequences ($w_\beta$), Number of Antigen Wells i.e., number of wells occupied by antigen sequences ($w_\delta$), Number of wells with Alpha, Beta, Antigen i.e., number of wells occupied by all three types of sequences ($w_{\alpha\beta\delta}$) and finally the Number of Simulations to run. FIG. 4, panel in the right displays the simulation results. The plot title shows the p-value obtained by simulation. The x-axis of the plot is the possible number of wells shared by all three types of sequences, y-axis is the probability of co-occurrence for all three types of sequences. The dotted vertical line in the plot identifies the number of wells shared by all three types of sequences ($w_{\alpha\beta\delta}$) input by the user.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

We claim:

1. A method for identifying a T cell receptor (TCR) and an epitope peptide that specifically binds the TCR, the method comprising:

a) providing a plurality of mixture partitions comprising a population of T cells, the T cells comprising a plurality of different TCRs having a TCR heavy chain encoded by a TCR heavy chain nucleic acid and a TCR light chain encoded by a TCR light chain nucleic acid, wherein individual mixture partitions of the plurality of mixture partitions comprise:

i) a portion of the population of T cells, wherein the portion of T cells comprises one or more TCRs that specifically bind to a portion of a plurality of epitope peptides present in the mixture partition;

ii) a plurality of partition-specific barcodes comprising nucleic acid sequences that uniquely identifies the partition; and iii) a plurality of epitope nucleic acids encoding the epitope peptides;

b) in the plurality of mixture partitions, generating barcoded nucleic acids by attaching the partition-specific barcodes to the TCR heavy chain, TCR light chain, and epitope nucleic acids;

c) pooling the barcoded nucleic acids to form a pooled mixture; and d) sequencing the barcoded nucleic acids in the pooled mixture and thereby identifying the sequence of the heavy and light chain of the TCR that specifically binds the epitope peptide and the sequence of the epitope peptide that specifically binds the TCR by identifying heavy and light chain nucleic acids and epitope nucleic acids having matching partition-specific barcodes e) determining a partition segregation pattern for a plurality of TCR heavy chains, TCR light chains, and epitope peptides by identifying TCR heavy chain nucleic acids that have identical protein coding sequences but different partition-specific barcodes, TCR light chain nucleic acids that have identical protein coding sequences but different partition-specific barcodes, and epitope nucleic acids that have identical protein coding sequences but different partition-specific barcodes;

f) determining from the partition segregation pattern, the number of partitions in which a TCR heavy chain, a TCR light chain, and an epitope nucleic acids co-segregate;

g) applying Formula 1:

$$P = P(w_{\alpha\beta\delta} \mid W, w_\alpha, w_\beta, w_\delta) = \frac{C(W, w_{\alpha\beta\delta}) \times |(w_\alpha - w_{\alpha\beta\delta}), (w_\beta - w_{\alpha\beta\delta}), (w_\delta - w_{\alpha\beta\delta}), (W - w_{\alpha\beta\delta})|}{C(W, w_\alpha) \times C(W, w_\beta) \times C(W, w_\delta)}$$

Wherein:

$C(W,w_\alpha)$ is the number of ways we can choose $w_\alpha$ partitions from W partitions≡

$$\binom{W}{w_\alpha}$$

$C(W,w_\beta)$ is the number of ways we can choose $w_\beta$ partitions from W partitions≡

$$\binom{W}{w_\beta}$$

$C(W,w_\delta)$ is the number of ways we can choose $w_\delta$ partitions from W partitions≡

$$\binom{W}{w_\delta}$$

$C(W,w_{\alpha\beta\delta})$ is the number of ways we can choose $w_{\alpha\beta\delta}$ partitions from W partitions≡

$$\binom{W}{w_{\alpha\beta\delta}}$$

to determine the probability (P) that the number of partitions in step f) has occurred by random chance;

h) classifying the TCR heavy chain, the TCR light chain, and the epitope nucleic acids as encoding a TCR and epitope peptide that specifically bind to each other if probability (P) falls below a preset threshold.

2. The method of claim 1, wherein the preset threshold is P=0.05.

* * * * *